United States Patent [19]
Koch

[11] Patent Number: 6,021,534
[45] Date of Patent: Feb. 8, 2000

[54] EAR LAVAGE AND EXAMINATION TABLE

[76] Inventor: Craig S. Koch, 6176 Reservoir Ct., Granite Bay, Calif. 95746

[21] Appl. No.: 09/063,855

[22] Filed: Apr. 21, 1998

[51] Int. Cl.[7] ....................................................... A47B 7/02
[52] U.S. Cl. ......................... 5/606; 5/634; 5/908; 108/24; 604/346; 604/355
[58] Field of Search ............................. 5/606, 633, 634, 5/638, 643, 652.1, 657, 908; 604/317, 322, 346, 355; 108/23, 24, 25, 26, 50.15

[56] References Cited

U.S. PATENT DOCUMENTS

| | | | |
|---|---|---|---|
| 1,584,139 | 5/1926 | Porter | 108/24 X |
| 3,808,615 | 5/1974 | Geary | 5/638 X |
| 4,751,620 | 6/1988 | Wright et al. | 108/23 X |
| 5,413,035 | 5/1995 | Fernandez | 108/24 X |

*Primary Examiner*—Terry Lee Melius
*Assistant Examiner*—James M Hewitt
*Attorney, Agent, or Firm*—Donald E. Nist

[57] ABSTRACT

The ear lavage and medical examination table includes an upper plate and a lower plate connected thereto at the rear ends of the two plates. The upper plate has a front head support portion with an ear lavage drain hole extending down therethrough. Preferably, the upper plate is curved or dished to comfortably support the torso of a patient. The lower plate is preferably horizontal while the upper plate rises thereabove at an angle from the rear end to the front end of the table. In one embodiment the two plates are integral and the angle is fixed. In another embodiment the two plates are interconnected so that the angle and distance therebetween can be adjusted. The table also includes a water catch tray supported on the upper surface of the lower plate directly below the upper plate hole and removeable therefrom for emptying. The tray bears a light and a mirror. The mirror can be secured to a flexible base support slideably disposed in an elongated slot in the tray for accurate positioning of the mirror. In one embodiment the mirror is secured to an upstanding wall of the tray. The table is light in weight and adapted to be placed on a lower support table or the like.

10 Claims, 1 Drawing Sheet

EAR LAVAGE AND EXAMINATION TABLE

BACKGROUND OF THE INVENTION

1. Field of the Invention

The present invention generally relates to medical equipment and more particularly to an ear lavage and medical examination table of an improved type.

2. Prior Art

Removal of cerumen (ear wax) is a frequent procedure in medical primary care. Foreign bodies are also occasionally removed from the ear canal of children. Ear cerumen frequently impedes examination of the ear drum in patients because it occludes the visual axis of the ear canal.

Any one or more of three methods are used to remove cerumen: curettage, suction and lavage, depending on circumstances. Curettage is often attempted initially. However, some cerumen impactions are very hard and desiccated and may not be removeable by curettage without applying significant pressure to the ear canal walls, resulting in considerable pain. Moreover, the inner half of the ear canal is very sensitive to touch. Cerumen in that area is usually difficult to remove with curettage because the curette often must touch that portion of the ear canal in order to perform the procedure. In addition, the cerumen tends to fragment into small dry and flaky particles that elude capture with the curette.

A suction apparatus often is not available in the office of a primary physician. Moreover, suction is noisy and may frighten children. When frightened a child may move suddenly and unpredictably, causing the suction apparatus to strike the ear canal wall, causing pain and impeding the procedure.

Therefore, lavage is preferred in many instances for the removal of cerumen. This is particularly the case when a frightened child is the patient and is struggling about. Introducing a rigid curette or suction apparatus into the ear canal under these circumstances is not viable. Although water impinging on the cerumen in the ear during lavage is much less traumatic, lavage has its own set of problems.

Thus, lavage is often attempted on infants and young childrn while holding them on a lap in the sitting position, which they usually resist at some point during the procedure. Moreover, it is preferred to have the ear canal directed downwardly to permit the cerumen and effluent water to drain quickly and completely from the ear canal. But it is very difficult to position an infant or young child so that the ear canal is directed downwardly while the patient is sitting. Also, when the head is tilted downwards it is difficult for the caregiver to align the the lavage nozzle with the ear canal axis.

In performing the lavage a water catch basin must be positioned near the ear. Although an adult patient can hold the basin, a young child or infant cannot do so and the parent must do so instead. However, the parent is also required to restrain the child or infant and this is best done with both hands, leaving no hands to hold the basin. The caregiver's both hands are required for proper operation of the lavage, one hand holding the irrigation syringe and the other hand holding the auricle to straigthen the ear canal. In many instances, the effluent water and cerumen particles are spilled from the catch basin, soaking the patient and the caregiver.

If the child or infant is positioned on a table, the ear canal is only an inch or two above the table level unless the patient's head is rotated upwardly, making removal of cerumen and effluent water from the ear canal difficult. Moreover, there usually is no room for a catch basin to be positioned to catch the cerumen and effluent from the ear canal so that the patient and table usually become soaked.

Accordingly, there is a need for an appliance which will make the ear lavage procedure easier, cleaner and more efficient.

The appliance should be capable of serving the lavage needs of adults, children and infants equally well. The appliance should be inexpensive and easily positioned and used with conventional ear lavage equipment.

SUMMARY OF THE EAR LAVAGE AND EXAMINATION TABLE OF THE INVENTION

The ear lavage and examination table of the present invention satisfies all the foregoing needs. Thus, the table is simple, inexpensive, durable, easy to use and permits ear lavage procedures to be carried out rapidly and efficiently without stress to the patient and the caregiver. Moreover, it allows the water and cerumen to be drained from the ear canal directly into a catch basin which forms part of the table, without spillage and without soaking the patient and the caregiver.

The table comprises, in combination, (a) an upper patient-supporting plate having a front head supporting end defining an ear lavage drain hole extending down therethrough, (b) a lower base support plate either integral with the upper plate or connected thereto so that the upper plate extends upwardly therefrom from the rear to the front thereof, and (c) a water catch tray removeably secured to the lower plate directly below the drain hole. The tray includes a light for viewing the ear canal and a mirror angled to permit the caregiver to view the lighted ear canal while standing or sitting above and to one side of the patient.

In one embodiment, the upper and lower plates are hinged together and the relative angle therebetween is adjustable by one or more struts or the like interconnecting the two plates. The lower plate is horizontal so that the table, which can be made relatively short, for example, about 3 feet long, can sit on a conventional examination table or gurney. The upper plate preferably is dished so as to comfortably cradle the torso or upper torso of the patient. Moreover, the upper and lower plate and the tray can be of metal, plastic or the like, and the tray can be supported on one or more tracks in the upper surface of the lower plate. If desired, the mirror can be adjustably positioned on a flexible support base, the lower end of which is slideably disposed in a slot in an upstanding wall of the tray.

Further features of the improved ear lavage and examination table of the present invention are set forth in the following detailed description and accompanying drawings.

DRAWINGS OF THE EMBODIMENTS OF THE INVENTION

FIG. 1 is a schematic top perspective view, partly broken away, of a first preferred embodiment of the improved ear lavage and examination table of the present invention; and, FIG. 2 is a schematic top perspective view, partly broken away, of a second preferred embodiment of the improved ear lavage and examination table of the present invention.

DETAILED DESCRIPTION OF THE EMBODIMENTS

FIG. 1

Figure 1:
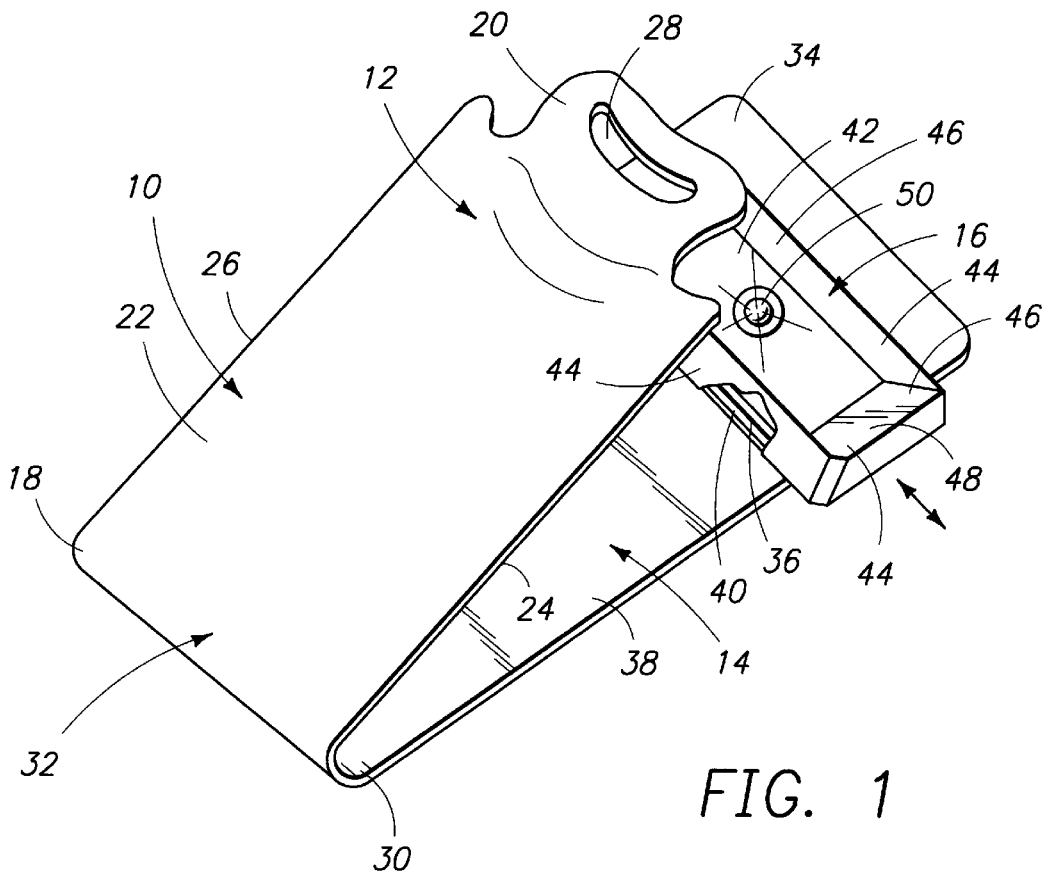

Now referring more particularly to FIG. 1 of the drawings, a first preferred embodiment of the improved ear lavage and examination table of the present invention is schematically depicted therein.

Thus, table 10 is shown which comprises, in combination, an upper plate 12, a lower plate 14 and a water catch basin or tray 16 removeably secured to lower plate 14. Upper plate 12 is elongated and of sufficient width to support the upper torso and head of an adult patient and the entire body of an infant or small child. It has a rear end 18, an opposite front end 20 and an intermediate portion 22 with opposite sides 24 and 26. Front end 20 has a water and cerumen drain hole 28 therein spaced inwardly from sides 24 and 26. Plate 12 is preferably dished or slightly concave so as to effectively cradle the torso and head of an adult and the body of a small child or infant.

Thus, plate 12 can be of any convenient length and width such as 1.5–2 feet in width and 3–4 feet or more in length. Other suitable dimensions are possible.

Lower plate 14 is preferably horizontal and of a width and length commensurate with upper plate 12. Rear end 30 of plate 14 is integral with rear end 18 of plate 12 and and forms therewith a rounded smooth end portion 32. Plate 12 rises from rear end 18 to front end 20 at a fixed angle to plate 14 and front end 34 of plate 14 has tray 16 removeably supported thereover, specifically on a track 36 integral with the upper surface 38 of plate 14 and disposed in a mating groove 40 in the closed bottom 42 of tray 16. Tray 16 can be slid sideways to remove it from table 10 for emptying, cleaning and replacing it after the lavage is completed.

Tray 16 has raised sides 44 with one or more downwardly and inwardly sloped surfaces 46, one of which supports an angled mirror 48, positoned such that the caregiver can view the ear canal of a patient lying on plate 12 with the ear canal directly over hole 28 while the caregiver is above and to one side of table 10. In order to facilitate such viewing, tray 16 also includes a light 50 powered by a battery (not shown) or interconnected to an electrical outlet (not shown), which light 50 is sealed in bottom 42 directly below hole 28 so that light 50 shines light beams directly into the ear canal through hole 28.

Accordingly, the head of the patient on tray 10 is cradled and properly supported and positioned for optimum ear lavage from below plate 12 by the caregiver. Water and cerumen draining from the ear canal during and after lavage falls though hole 28 directly into tray 16 without splashing on the patient or the caregiver. The lavage procedure is thus rapidly and efficiently carried out without stress to either the patient or the caregiver.

Table 10, including plates 12 and 14 and tray 16 can be readily and inexpensively fabricated from plastic, metal, wood, ceramic or other suitable material and can be of any suitable size.

FIG. 2

Figure 2:
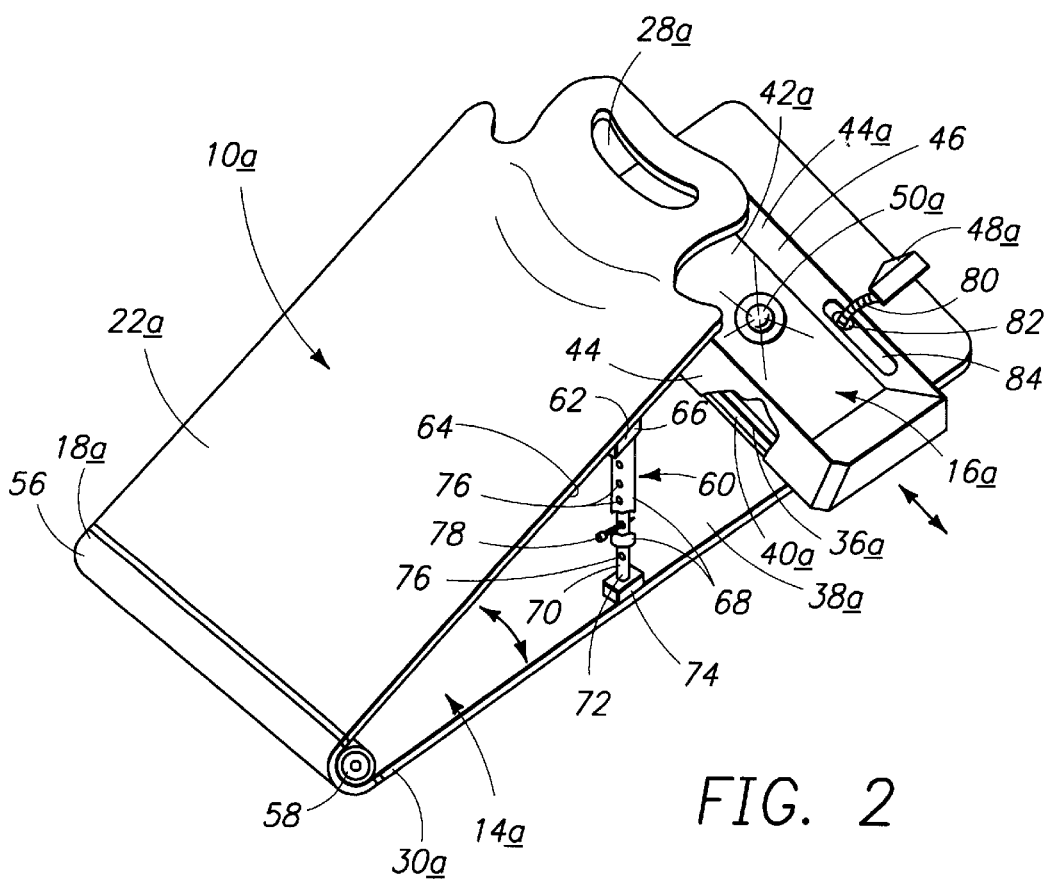

A second preferred embodiment of the improved ear lavage and examination table of the present invention is schematically depicted in FIG. 2. Thus, table 10a is shown. Components thereof similar to those of table 10 bear the same numerals but are succeeded by the letter "a".

Table 10a differs from table only as follows:

a) Plates 12a and 14a are separate from one another but interconnected through hinge means in the form of a flexible resilient curved elastomeric strip 56 bonded to ends 18a and 30a and disposed around and connected to a transversely extending cylindrical dowel 58 so that the angle between plate 12a and plate 14a can be changed easily.

b) The angle of inclination between plate 12a and plate 14a can be decreased and increased by adjusting telescoping strut 60 the upper end 62 of which is secured to the underside 64 of plate 12a by a fitting 66 and which includes a hollow depending tube 68 which receives a mating tubular upraised tube 70 secured at its lower end 72 to a fitting 74 secured to the upper surface 38a of plate 14a. Tubes 68 and 70 have alignable openings 76 through which a removable pin 78 is inserted to adjust the height of plate 12a above plate 14a. Preferably, there are a pair of struts 60 disposed on opposite sides of table 10a.

c) Mirror 48a is supported above tray 16a on a flexible upstanding neck 80, the lower end 82 of which is slideably disposed in a longitudinal groove 84 in a side 44a of tray 16a so that mirror 48a can be adjusted in position relative to tray 16a and in angle to tray 16a for optimal positioning for viewing the ear canal of the patient through drain hole 28a.

Table 10a has the other advantages of table 10.

Various other modifications, changes, alterations and additions can be made in the improved ear lavage and examination table of the present invention, its components and parameters. All such modifications, changes, alterations and additions as are within the scope of the appended claims form part of the present invention.

What is claimed is:

1. A table for ear lavage and medical examination of an ear canal of a human patient having a torso, said table comprising, in combination:

a) an upper patient-supporting elongated plate having a front head-supporting end defining an ear lavage drain hole extending downwardly therethrough and an opposite rear end;

b) a lower flat elongated plate disposed below and connected to and supporting said upper plate, said lower plate having an upper surface, an opposite lower surface and a front end and opposite rear end; and, c) a water catch tray removeably secured to said lower plate upper surface at said lower plate front end and positioned directly below said drain hole, said catch tray having an upper surface and a mirror and light secured to said tray for lighting the ear canal of the human patient when said patient is on said upper plate and for viewing said ear canal when lighted by a care-giver positioned above and to one side of said upper plate, whereby ear lavage and medical examination of a patient on said upper plate are readily carried out.

2. The ear lavage and medical examination table of claim 1 wherein said upper and lower plates are integral.

3. The ear lavage and medical examination table of claim 1 wherein said upper and lower plates are secured together by a connector.

4. The ear lavage and medical examination table of claim 3 wherein said upper and lower plates are hinged together at their rear ends for adjusting an angle and distance between said plates.

5. The ear lavage and medical examination table of claim 3 wherein said upper plate slopes upwardly from its rear end to its front end, relative to said lower plate.

6. The ear lavage and medical examination table of claim 5 wherein said lower plate is about horizontal and wherein said angle and distance between said upper plate and said lower plate are adjustable by the connector connected to said upper and lower plates.

7. The ear lavage and medical examination table of claim 1 wherein said upper plate is dished for improved support of a patient.

8. The ear lavage and medical examination table of claim 1 wherein said upper plate is adapted to support said torso and wherein said table is adapted to be placed on top of a support base.

9. The ear lavage and medical examination table of claim 1 wherein said tray is slideably disposed on at least one rail defined in the upper surface of said lower plate and wherein said tray has at least one upraised end wall to which said mirror is secured.

10. The ear lavage and medical examination table of claim 1 wherein said mirror includes an elongated flexible base support slideably disposed in an elongated groove in the upper surface of said tray for adjustably positioning said mirror for optimal viewing.

* * * * *